US012121288B2

(12) United States Patent
Forsyth et al.

(10) Patent No.: US 12,121,288 B2
(45) Date of Patent: Oct. 22, 2024

(54) COMBINATION TUMOR TREATMENT

(71) Applicants: Boston Scientific Scimed, Inc., Maple Grove, MN (US); REGENTS OF THE UNIVERSITY OF MINNESOTA, Minneapolis, MN (US)

(72) Inventors: Bruce R. Forsyth, Hanover, MN (US); Chun Wang, Minneapolis, MN (US); Samuel Hanson, Minneapolis, MN (US)

(73) Assignees: Boston Scientific Scimed, Inc., Maple Grove, MN (US); Regents of the University of Minnesota, Minneapolis, MN (US)

( * ) Notice: Subject to any disclaimer, the term of this patent is extended or adjusted under 35 U.S.C. 154(b) by 545 days.

(21) Appl. No.: 17/204,150

(22) Filed: Mar. 17, 2021

(65) Prior Publication Data

US 2021/0290300 A1 Sep. 23, 2021

Related U.S. Application Data

(60) Provisional application No. 62/991,298, filed on Mar. 18, 2020.

(51) Int. Cl.
*A61B 18/14* (2006.01)
*A61B 18/00* (2006.01)
*A61L 27/36* (2006.01)

(52) U.S. Cl.
CPC ...... *A61B 18/1477* (2013.01); *A61B 18/1485* (2013.01); *A61L 27/3641* (2013.01); *A61B 2018/00154* (2013.01); *A61B 2018/00333* (2013.01); *A61B 2018/00345* (2013.01); *A61B 2018/00452* (2013.01); *A61B 2018/00494* (2013.01); *A61B 2018/00511* (2013.01); *A61B 2018/00529* (2013.01); *A61B 2018/00541* (2013.01); *A61B 2018/00547* (2013.01);

(Continued)

(58) Field of Classification Search
None
See application file for complete search history.

(56) References Cited

U.S. PATENT DOCUMENTS 5,733,572 A * 3/1998 Unger .................. A61K 9/127
424/9.4
2003/0212022 A1 * 11/2003 Vogel .................. A61K 9/0019
514/44 R (Continued)

OTHER PUBLICATIONS

Google_Scholar_Search_String_1 (Year: 2024).*

(Continued)

*Primary Examiner* — Ronald Hupczey, Jr.
*Assistant Examiner* — Nicholas S Borsch
(74) *Attorney, Agent, or Firm* — Seager, Tufte & Wickhem, LLP (57) ABSTRACT

In some aspects, the present disclosure pertains to methods of treating a tissue volume comprising (a) administering an implantable composition comprising a releasable membrane-active agent to a target site such that the membrane-active agent is locally released to the tissue volume and (b) performing irreversible, reversible and/or thermal treatment by application of a pulsed electric field to the tissue volume. In other aspects, the present disclosure pertains to embolic compositions that comprise releasable membrane-active agents.

17 Claims, 7 Drawing Sheets

(52) U.S. Cl.
CPC ........... *A61B 2018/00559* (2013.01); *A61B 2018/00613* (2013.01); *A61L 2400/06* (2013.01)

(56) References Cited

U.S. PATENT DOCUMENTS

| | | | |
|---|---|---|---|
| 2004/0092825 A1* | 5/2004 | Madar | A61N 1/327 604/890.1 |
| 2009/0169471 A1 | 7/2009 | Richard et al. | |
| 2011/0104052 A1* | 5/2011 | Barnett | A61K 9/1635 424/1.25 |
| 2012/0089009 A1 | 4/2012 | Omary et al. | |
| 2015/0080940 A1 | 3/2015 | Gemborys | |
| 2018/0055516 A1* | 3/2018 | Baldwin | A61B 17/12181 |
| 2019/0143106 A1 | 5/2019 | Dewitt et al. | |

OTHER PUBLICATIONS

Google_Scholar_Search_String_2 (Year: 2024).*
Google_Scholar_Search_String_3 (Year: 2024).*
Lord Jasmine et al: "Advancements in the development on new liquid embolic agents for use in therapeutic embolisation", Journal of Materials Chemistry. B, vol. 8, No. 36, Aug. 7, 2020, pp. 8207-8218.
Wang Chun: "A Synergistic therapy for multi-drug resistant cancers", Technology—No. 2019-141, Jan. 18, 2021, pp. 1-3.
Jingjie Hu et al: "Advances in Biomaterials and Technologies for Vascular Embolization" Advanced Materials, Jan. 1, 2019, pp. 1-52.
Palermo Edmund F. et al.: "Cationic Spacer Arm Design Strategy for Control of Antimicrobial Activity and Conformation of Amphiphilic Methacrylate Random Copolymers", Biomacromolecules, vol. 13, No. 5, May 14, 2012, pp. 1632-1641.
International Search Report and Written Opinion for the International Patent Application No. PCT/US2021/022705, mailed Jul. 15, 2021, 19 pages.
Chan P, McLean C, Chan S, Goh GS. The interaction between irreversible electroporation therapy (IRE) and embolization material using a validated vegetal model: an experimental study. Diagn Interv Radiol. 2019;25(4):304-309. doi: 10.5152/dir.2019.18361.
Gabernet, G., Gautschi, D., Muller, A.T. et al. In silico design and optimization of selective membranolytic anticancer peptides. Sci Rep 9, 11282 (2019) doi:10.1038/s41598-019-47568-9.
Kovalainen et al., "Novel Delivery Systems for Improving the Clinical Use of Peptides" Pharmacological Reviews 67:541-561, Jul. 2015.
Gaspar, Diana et al. "From antimicrobial to anticancer peptides. A review." Frontiers in microbiology vol. 4 294. Oct. 1, 2013, doi: 10.3389/fmicb.2013.00294.
Chen Y, Moser MAJ, Luo Y, Zhang W, Zhang B. Chemical Enhancement of Irreversible Electroporation: A Review and Future Suggestions. Technol Cancer Res Treat. 2019;18:1533033819874128. doi: 10.1177/1533033819874128.
Weihang Ji, "Synthetic Polymers With Well-Defined Structures for DNA Vaccine Delivery and Cancer Therapy", Libraries digital conservancy, p. iii, 89,95, Nov. 11, 2013.

* cited by examiner

COMBINATION TUMOR TREATMENT

PRIORITY

The present application is a non-provisional of, and claims the benefit of priority under 35 U.S.C. § 119 to, U.S. Provisional Application Ser. No. 62/991,298, filed Mar. 18, 2020, the disclosure of which is herein incorporated herein by reference in its entirety.

FIELD

The present disclosure pertains to methods for tumor treatment and to compositions for use in tumor treatment.

BACKGROUND

A number of modalities are used to treat abnormal biological tissue such as cancer, including thermal ablation, cryoablation, ultrasonic ablation, chemical ablation, RF electrical ablation, and irreversible electroporation.

New and different approaches to biological tissue destruction are desired. The present disclosure describes new compositions and combination approaches for tissue destruction using irreversible electroporation.

SUMMARY

In some aspects, the present discloses methods of treating a tissue volume that comprise (a) administering an implantable composition comprising a releasable membrane-active agent to a target site such that the membrane-active agent is locally released to the tissue volume and (b) performing treatment of the tissue volume by application of a pulsed electric field to the tissue volume. For example, irreversible electroporation, reversible electroporation and/or thermal treatment may be performed by application of the pulsed electric field.

As used herein, a "membrane-active agent" is defined as agent or molecule that affects the architecture and dynamics of a cellular membrane, such as cationic or amphiphilic or anionic molecules. Cationic molecules bind to cell membrane via charge-charge attraction. Amphiphilic molecules bind to cell membrane via charged functional groups and with cell membrane lipids via hydrophobic interaction. Anionic molecules upon protonation may become hydrophobic and interact with cell membrane lipids. As used herein a "membranolytic agent" is a subset of membrane-active agents which refers to an agent or molecule that disrupts the membrane integrity. Membrane-active agents often become membranolytic when present at sufficiently high concentrations.

In some embodiments, the tissue volume corresponds to all or part of a tumor and/or healthy tissue surrounding the tumor (to create a margin via the vasculature). Examples of tumors include tumors of the pancreas, breast, lung, prostate, liver, kidney, brain, uterus, ovary, stomach, duodenum, or skin.

In some embodiments, which may be used in conjunction with any of the above aspects and embodiments, the implantable composition is an embolic composition comprising the releasable membrane-active agent, and the embolic composition is administered to one or more blood vessels that supply blood the tissue volume or the embolic composition is administered percutaneously or endoscopically via injection.

In some embodiments, which may be used in conjunction with any of the above aspects and embodiments, the implantable composition is a liquid composition that becomes a solid implant upon introduction into the body. For example, the implantable composition may be a gel having viscoelastic properties that is administrated as a liquid and changes to solid upon activation or body fluid contact.

In some embodiments, which may be used in conjunction with any of the above aspects and embodiments, the administered implantable composition is at least partially biostable or is bioabsorbable.

In some embodiments, which may be used in conjunction with any of the above aspects and embodiments, the implantable composition is a solid implantable composition.

In some embodiments, which may be used in conjunction with any of the above aspects and embodiments, solid implantable composition is an implantable particle. In some of these embodiments, the particle may range from 10 nm to 10 mm (e.g., ranging from 10 nm to 100 nm to 1000 nm to 10 microns to 100 microns to 1000 microns to 10 mm) in maximum cross-sectional dimension.

In some embodiments, which may be used in conjunction with any of the above aspects and embodiments, the solid embolic composition may be a scaffold. Examples of scaffolds include, for example, a disc, a rod, a stent, a coil, a fiducial marker, a plate, a tube, or a semi-permeable woven mesh.

In some embodiments, which may be used in conjunction with any of the above aspects and embodiments, the membrane-active agent is present throughout the solid implantable composition, or the membrane-active agent is present in only a portion of the solid implantable composition.

In some embodiments, which may be used in conjunction with any of the above aspects and embodiments, the membrane-active agent is present at a surface of the solid implantable composition but is not present in a bulk of the solid implantable composition, or the membrane-active agent is present in a bulk of the solid implantable composition but is not present at a surface of the solid implantable composition, or the membrane-active agent is homogeneously present in the solid implantable composition, or the membrane-active agent is present in a concentration gradient the solid implantable composition.

In some embodiments, which may be used in conjunction with any of the above aspects and embodiments, the membrane-active agent is present in one or more layers disposed on an underlying substrate material, or the membrane-active agent is encapsulated within an encapsulating material, or the membrane-active agent is dispersed within a matrix material.

In some embodiments, which may be used in conjunction with any of the above aspects and embodiments, the membrane-active agent is coated on or infused into an embolic bead or conjugated to an embolic bead via a covalent linkage.

In some embodiments, which may be used in conjunction with any of the above aspects and embodiments, the membrane-active agent is selected from cationic molecules, amphiphilic molecules, and anionic molecules. For example, the membrane-active agent may be selected from cationic polymers, anionic polymers and amphiphilic polymers.

In some embodiments, which may be used in conjunction with any of the above aspects and embodiments, the membrane-active agent may be locally released to the tissue volume in a burst release profile, the membrane-active agent may be locally released to the tissue volume in a sustained release profile, or the membrane-active agent may be locally released to the tissue volume in a combination of a burst release profile and a sustained release profile.

In some embodiments, which may be used in conjunction with any of the above aspects and embodiments, release of the membrane-active agent is triggered by electrical pulses, ultrasound, magnetic field variations, or thermal inputs.

In some embodiments, which may be used in conjunction with any of the above aspects and embodiments, the treatment is performed in a same procedure as administration of the implantable composition.

In some embodiments, which may be used in conjunction with any of the above aspects and embodiments, the treatment is performed in a procedure subsequent to administration of the implantable composition.

In some embodiments, which may be used in conjunction with any of the above aspects and embodiments, the treatment is performed in a procedure at a time ranging from the same day, the next day, or a time ranging from 2 days to 1 week to 2 weeks to 30 days after administration of the implantable composition.

In some embodiments, which may be used in conjunction with any of the above aspects and embodiments, one or more electrodes for the treatment are placed within or adjacent to the tissue volume.

In some embodiments, which may be used in conjunction with any of the above aspects and embodiments, (a) one or electrodes for the treatment are placed adjacent the tissue volume at one or more locations on the skin, (b) one or electrodes for the treatment are percutaneously placed within or adjacent to the tissue volume, (c) one or electrodes for the treatment are placed within or adjacent to the tissue volume via a device that is inserted into one or more natural body lumens, or (d) a combination of any two or all three of the preceding placement techniques.

Other aspects of the present disclosure pertain to embolic compositions that comprise releasable membrane-active agent.

In some of these embodiments, the embolic composition is a solid embolic composition.

In some of these embodiments, the embolic composition is a liquid composition that becomes a solid embolic composition upon introduction into the body. For example, the embolic composition may be gel having viscoelastic properties that is administrated as a liquid and changes to solid upon activation or body fluid contact In some embodiments, which may be used in conjunction with any of the above aspects and embodiments, the solid embolic composition is at least partially biostable or is bioabsorbable.

In some embodiments, which may be used in conjunction with any of the above aspects and embodiments, the solid embolic composition is an implantable particle. In some of these embodiments, the particle may range from 10 nm to 10 mm in maximum cross-sectional dimension.

In some embodiments, which may be used in conjunction with any of the above aspects and embodiments, the solid embolic composition is a scaffold.

In some embodiments, which may be used in conjunction with any of the above aspects and embodiments, the membrane-active agent is present throughout the solid embolic composition or the membrane-active agent is present in only a portion of the solid embolic composition.

In some embodiments, which may be used in conjunction with any of the above aspects and embodiments, the membrane-active agent is present at a surface of the solid embolic composition but is not is present in a bulk of the solid embolic composition, the membrane-active agent is present in a bulk of the solid embolic composition but is not is present at a surface of the solid embolic composition, the membrane-active agent is homogeneously present in the solid embolic composition, or the membrane-active agent is present in a concentration gradient in the solid embolic composition.

In some embodiments, which may be used in conjunction with any of the above aspects and embodiments, the membrane-active agent is present in one or more layers disposed on an underlying substrate material, the membrane-active agent is encapsulated within an encapsulating material, the membrane-active agent is dispersed within a matrix material, or the membrane-active agent is or conjugated to a matrix material.

In some embodiments, which may be used in conjunction with any of the above aspects and embodiments, the membrane-active agent is selected from cationic molecules, amphiphilic molecules, and anionic molecules. For example, the membrane-active agent may be selected from cationic polymers, anionic polymers and amphiphilic polymers.

In some embodiments, which may be used in conjunction with any of the above aspects and embodiments, upon implantation of the embolic composition in a subject, the membrane-active agent is locally released in a burst release profile, in a sustained release profile, or in a combination of a burst release profile and a sustained release profile.

Additional aspects and embodiments of the disclosure will become apparent to those of ordinary skill in the art upon review of the Detailed Description to follow.

BRIEF DESCRIPTION OF THE DRAWINGS

FIGS. 1A-1D show microspheres coated with fluorescently labeled PAHM. (FIG. 1B) Fluorescence intensity of PAHM coating on individual microspheres.

FIGS. 2A and 2B illustrate quantification of PAHM in cell culture medium. (FIG. 2A) UV-Vis absorption spectra of different PAHM concentrations. (FIG. 2B) Calibration curve of absorbance at 245 nm vs. PAHM concentration.

FIGS. 5A-5F show cell viability after IRE treatment combined with PAHM exposure for (FIG. 5A) 15 min (FIG. 5B) 4 h (FIG. 5C) 24 h. Data are shown as mean+/−SD (n=3-12). ANOVA with Tukey HSD test (*$p<0.05$, $p<0.01$, *$p<0.001$, ***$p<0.0001$).

FIGS. 8A-8F show cell viability after IRE treatment combined with exposure to PAHM released from coated microspheres for (FIG. 8A) 15 min (FIG. 8B) 4 h (FIG. 8C) 24 h. Data are shown as mean+/−SD (n=3-9). ANOVA with Tukey HSD test (*p<0.05, p<0.01, *p<0.001, ****p<0.0001). (FIG. 8D) Combination index analysis (CI<1, =0.9-1 (dashed lines), >1 indicates synergism, nearly additive effect, and antagonism, respectively). Dose reduction index analysis for (FIG. 8E) IRE and (FIG. 8F) microsphere-coated PAHM (DRI<1, =1 (dashed line), >1 indicates unfavorable dose reduction, no dose reduction, favorable dose reduction, respectively).

DETAILED DESCRIPTION

Electroporation is a phenomenon in which a biological cell responds to electrical fields by opening pores in the cellular membrane. At low electric field strength, no pores form in the cellular membrane. Above an electroporation threshold, pores begin to reversibly form. Reversible electroporation has long been used to introduce material to biological cells that would not otherwise be able to pass through the cellular membrane. For example, genetic material or large molecules used in chemotherapy may be introduced to the interior of a cell. After removal of the electrical field, the induced pores close in "transient" or "reversible" electroporation.

At relatively higher amplitude electroporation doses, the pores that form in response to the applied electrical field can become so extensive that the cell membrane cannot recover. If the cell membrane does not recover, the cell will die due to this electroporation, known as "irreversible" electroporation. The thresholds for irreversible electroporation (IRE) vary with cell size and shape, overall tissue structure, and intercellular fluid characteristics. The thresholds themselves can be defined by local electric field strength and duration, for example where a higher amplitude voltage is needed at shorter durations, and lower amplitude voltage is needed at longer durations.

In the present disclosure, methods of treating a tissue volume are described that comprise (a) administering an implantable composition comprising a releasable membrane-active agent to a target site, such that the membrane-active agent is locally released to a tissue volume and (b) performing IRE on the tissue volume During electroporation treatments in accordance with the present disclosure, a voltage is applied across two or more electrodes that are positioned within or adjacent to a tissue volume that is to be treated, thereby creating an electrical field in the tissue volume. Parameters that can be adjusted in IRE include voltage magnitude, voltage duration (pulse length), number of pulses, number of electrodes, and electrode spacing.

Tissue volumes to which irreversible electroporation treatments in accordance with the present disclosure may be applied include benign and malignant tumor volumes, and perfused or healthy tissue volumes that include viably functioning cells that make up a demarcated tumor volume. Examples of tumor volumes include those present in pancreatic tumors, esophageal tumors, bladder tumors, biliary tumors, liver tumors, kidney tumors, breast tumors, lung tumors, prostate tumors, brain tumors, uterine tumors including uterine fibroids, ovarian tumors, retroperitoneal tumors, extremity tumors, pelvic tumors, as well as neuroendocrine tumors or pre-cancerous hyperplastic cell clusters or neoplastic structures.

A wide range of irreversible electroporation settings may be used in conjunction with the irreversible electroporation treatments of the present disclosure, including voltages that provide electric field strengths ranging from 250-2500 V/cm, more typically 375-1750 V/cm, number of pulses ranging from 1 to 5000, more typically, 5-300, pulse widths ranging from 0.5 to 1000 μs, more typically 1 to 250 μs, pulse frequency ranging from 0.25 to 10 Hz, and electrode spacing ranging from 0.1 to 2 cm. Electrodes may be operated in monopolar mode, bipolar mode or multiplexed configurations across multiple electrode combinations or probes.

Electrodes may be placed within or adjacent to a tissue volume that is to be treated by irreversible electroporation using various methods, including (a) placement of one or more electrodes on one or more locations of the skin (including return electrode placement), (b) percutaneous electrode placement of one or more electrodes in one or more tissue locations, (c) placement of one or more electrodes in or adjacent to one or more natural body lumens (e.g., blood vessels, gastrointestinal tracts, biliary ducts, lymph ducts, urinary tracts, pulmonary airways, urethral spaces, bladders, or other body lumens), or (d) a combination of any two or all three of these placement techniques.

With regard to placement of one or more electrodes in or adjacent to a natural body lumen, a device such as a catheter, an endoscope, bronchoscope, duodenoscope or similar minimally invasive, single use or reusable direct visualization probe may be advanced into the body lumen, in which case one or more electrodes may be positioned on the device and brought into contact with a lumen wall, or one or more electrodes may be inserted from the device, through a lumen wall that is proximate the device, and into the tissue surrounding the lumen wall.

As previously noted, in the present disclosure, methods of treating a tissue volume are described that comprise (a) administering an implantable composition comprising a releasable membrane-active agent to a target site, such that the membrane-active agent is locally released to a tissue volume and (b) performing IRE on the tissue volume. In this regard, the membrane-active agents may be used to increase the number of cells that are killed at a given electric field strength and/or decrease the electric field strength required to kill a given number of cells.

The membrane-active-agent-releasing implantable composition may be selected from membrane-active-agent-releasing implantable compositions that are at least partially biostable and membrane-active-agent-releasing implantable compositions that are bioabsorbable.

In some embodiments, the membrane-active-agent-releasing implantable composition may be an embolic composition that comprises the membrane-active agent, and the embolic composition may be administered to one or more blood vessels that supply blood to the tissue volume, thereby forming an embolus/occlusion. In this way, the methods of the present disclosure may kill cells by cutting off the blood supply of the cells, in addition to killing cells by membrane-active agent-enhanced IRE.

Examples of membrane-active agents include cationic molecules, amphiphilic molecules, and anionic molecules.

Membrane-active cationic molecules may be selected from natural and synthetic cationic polymers having primary, secondary, tertiary or quaternary amine groups.

Natural cationic polymers include cationic polypeptides (such as polylysine, polyarginine and polyornithine), cationic polyamines (such as spermidine and spermine and their derivatives), cationic polysaccharides (such as chitosan and cationic gelatin), cationic peptides rich in cationic amino acids including lysine and arginine (such as cecropin A, magainins, dermaseptin, bombinin, mellitin, cathelicidin, human defensins, lactoferricin, histatin, indolicidin, tritripticin, holotricin, coleoptericin, pyrrhocoricin, etc.).

Synthetic cationic polymers are polymers containing primary, secondary, tertiary or quaternary amine groups. These polymers may contain molecular segments of linear, block, graft, branched, dendritic and network architectures. These cationic polymers may be selected from the classes of polyacrylates, polymethacrylates, polyacrylamides, polymethacrylamides, polyamides, polyesters, polyorthoesters, poly(beta-amino esters), polyethylenimine, polypropylenimine, polyamidoamine, polynorbornene, and their copolymers. They may be synthesized via free radical polymerization, ring-opening polymerization, polyaddition and polycondensation reactions. Synthetic cationic polymers also include cationic peptides with non-natural sequences that can bind to cell membrane. Such cationic peptides are rich in lysine and arginine and can be synthesized using solid-phase methods well known to the field.

Membranolytic amphiphilic molecules include the aforementioned natural and synthetic cationic polymers modified with hydrophobic groups and structures such as linear, branched, cyclic, aromatic hydrocarbons containing saturated and unsaturated C—C bonds. Membrane-active amphiphilic molecules also include the aforementioned cationic peptides containing hydrophobic amino acids (such as alanine, glycine, leucine, isoleucine, phenoalanine, tyrosine, tryptophan) or hydrophobic structures (such as hydrocarbone).

Membrane-active anionic molecules include certain carboxylic acid-containing synthetic polymers (such as polyalkyl acrylic acids) and peptides (such as "GALA": WEAA-LAEALAEALAEHLAEALAEALEALAA). These polymers and peptides protonate at acidic pH, become hydrophobic, and adopt conformations that facilitate interaction with cell lipid membrane.

Membranolytic agents are particular membrane-active agents that causes cell membrane disruption. Examples include amino alkyl acrylates such as amino-$C_2$-$C_{10}$ alkyl acrylates, amino alkyl methacrylates such as amino-$C_2$-$C_{10}$ alkyl methacrylates, and copolymers of amino alkyl acrylates with alkyl acrylates, and copolymers of amino alkyl methacrylates with alkyl methacrylates. Examples of membranolytic amino alkyl methacrylates include poly(6-aminohexyl methacrylate) (PAHM), poly(aminoethyl-co-butyl methacrylate), and poly(2-hexamethyleneimino)ethyl methacrylate.

In various embodiments, the membrane-active-agent-releasing implantable composition may be a liquid composition that becomes a solid membrane-active-agent-releasing implant upon introduction into the body (e.g., the composition may be in the form of a liquid embolic composition).

In various embodiments, the membrane-active-agent-releasing implantable composition may be a solid composition. Membrane-active agent may be located throughout the solid composition or in only a portion of the solid composition. For example, membrane-active agent may be present in one or more layers on an underlying substrate material (e.g., the layer(s) may be formed entirely from membrane-active agent or may be admixed with one or more additional bioabsorbable or biostable matrix materials from which the membrane-active agent is released), membrane-active agent may be encapsulated within an encapsulating material (e.g. a bioabsorbable encapsulating material or a biostable encapsulating material that is permeable to the membrane-active agent), membrane-active agent may be dispersed within a substrate material (e.g., by imbibing the substrate material membrane-active agent into a preexisting substrate material, by forming the substrate as a matrix that contains the membrane-active agent, etc.), membrane-active agents may be attached to one or more of the solid compositions via covalent linkages (such as amide, ester, ether, thiol ester, dithiol, ortho ester, acetal, ketal) from which the membrane-active agent is released, membrane-active agents may be attached to one of more of the solid compositions via noncovalent linkages (such as biotin-avidin, metal chelates, charge-charge electrostatic interactions, host-guest complexes such as polyethylene glycol/cyclodextrin, adamantane/cyclodextrin) from which the membrane-active agent is released, or by forming the solid composition entirely from membrane-active agent.

Thus, in addition to membrane-active agent, the implantable composition of the present disclosure may include substrate materials, matrix materials and encapsulating materials which may be bioabsorbable and/or biostable. Examples of bioabsorbable and/or biostable materials include bioabsorbable and/or biostable polymers, bioabsorbable and/or biostable metals and metal alloys, and bioabsorbable and/or biostable ceramic and glass materials.

Bioabsorbable and biostable polymers for use herein, as well as polymeric membrane-active agents, include homopolymers and copolymers. As used herein, "homopolymers" are polymers that contain multiple copies of a single constitutional unit. "Copolymers" are polymers that contain multiple copies of at least two dissimilar constitutional units, examples of which include random, statistical, gradient, periodic (e.g., alternating) and block (e.g., di-block, tri-block, etc.) copolymers. Polymers for use in the present disclosure can be linear or branched. Branched configurations include star-shaped configurations (e.g., configurations in which three or more chains emanate from a single branch point), comb configurations (e.g., configurations having a main chain and a plurality of side chains), dendritic configurations (e.g., arborescent and hyperbranched polymers), and so forth.

Specific examples of bioabsorbable and biostable polymers may be selected, for example, from the following: polycarboxylic acid homopolymers and copolymers including polyacrylic acid, alkyl acrylate and alkyl methacrylate homopolymers and copolymers, including poly(methyl methacrylate-b-n-butyl acrylate-b-methyl methacrylate) and poly(styrene-b-n-butyl acrylate-b-styrene) triblock copolymers, polyamides including nylon 6,6, nylon 12, and polyether-block-polyamide copolymers (e.g., Pebax® resins), vinyl homopolymers and copolymers including polyvinyl alcohol, polyvinylpyrrolidone, polyvinyl halides such as polyvinyl chlorides and ethylene-vinyl acetate copolymers (EVA), vinyl aromatic homopolymers and copolymers such as polystyrene, styrene-maleic anhydride copolymers, vinyl aromatic-alkene copolymers including styrene-butadiene copolymers, styrene-ethylene-butylene copolymers (e.g., a poly(styrene-b-ethylene/butylene-b-styrene (SEBS) copolymer, available as Kraton® G series polymers), styrene-isoprene copolymers (e.g., poly(styrene-b-isoprene-b-styrene), acrylonitrile-styrene copolymers, acrylonitrile-butadiene-styrene copolymers, styrene-butadiene copolymers and styrene-isobutylene copolymers (e.g., polyisobutylene-polystyrene block copolymers such as poly(styrene-b-isobutylene-b-styrene) or SIBS, which is described, for instance, in U.S. Pat. No. 6,545,097 to Pinchuk et al.), ionomers, polyesters including polyethylene terephthalate and aliphatic polyesters such as homopolymers and copolymers of lactide (which includes d-,l- and meso-lactide) (e.g., poly(L-lactide) and poly(d,l-lactide), glycolide (glycolic acid), and epsilon-caprolactone, including poly(lactide-co-glycolides) such as poly(l-lactide-co-glycolide) and poly(d,l-lactide-co-glycolide), polycarbonates including trimethylene carbonate (and its alkyl derivatives), polyanhydrides, polyorthoesters, polyether homopolymers and copolymers including polyalkylene oxide polymers such as polyethylene oxide (PEO) and polyether ether ketones, polyolefin homopolymers and copolymers, including polyalkylenes such as polypropylene, polyethylene, polybutylenes (such as polybut-1-ene and polyisobutylene), polyolefin elastomers (e.g., santoprene) and ethylene propylene diene monomer (EPDM) rubbers, fluorinated homopolymers and copolymers, including polytetrafluoroethylene (PTFE), poly(tetrafluoroethylene-co-hexafluoropropene) (FEP), modified ethylene-tetrafluoroethylene copolymers (ETFE) and polyvinylidene fluoride (PVDF), silicone homopolymers and copolymers including polydimethylsiloxane, polyurethanes, biopolymers such as polypeptides, proteins, polysaccharides, fibrin, fibrinogen, collagen, elastin, chitosan, gelatin, starch, and glycosaminoglycans such as hyaluronic acid; as well as blends and further copolymers of the above.

Examples of biostable polymers for use in the present disclosure may also be selected, for example, from homopolymers and copolymers containing one or more olefin monomers including fluorinated olefin monomers, acrylate monomers, methacrylate monomers, vinyl monomers, dialkylsiloxane monomers and combinations thereof as well as various other polymers including polyurethanes, polyureas, polyamides including nylons, polycarbonates, polyesters, poly(ether ketone) (PEEK), and poly(arylene ether ketone) PAEK.

Examples of bioabsorbable polymers for use in the present disclosure may also be selected from biodegradable polyester homopolymers and copolymers, poly(ortho ester) homopolymers and copolymers, polyanhydride homopolymers and copolymers, amino-acid-based homopolymers and copolymers including tyrosine-based polymers, and polyethylene glycol homopolymers and copolymers.

The membrane-active agent may be released from the implantable composition by diffusion, dissolution, biodegradation, including any type of chemical reaction such as hydrolysis (via covalent linkages) or enzymatic cleavage of bonds, ionization and deionization, or a combination of any of the foregoing.

The membrane-active agent may be released from the implantable composition in a burst release profile (e.g., within a time period of 0 to 6 hours), a sustained release profile (e.g., over a time period ranging from 6 hours to 3 months), a pulsatile release profile, a biphasic or multiphasic release profile, or a combination of the foregoing.

The membrane-active agent may be released from the implantable composition via a triggerable release mechanism, for example, as a result of electrical pulses (e.g., to heat the implantable composition, either with or without a corresponding phase transition, to drive the membrane-active agent from the implantable composition by electrical migration, etc.), ultrasound (e.g., which can be used to heat the implantable composition or to burst capsules that contain the membrane-active agent thereby releasing the membrane-active agent, etc.), magnetic field variations (e.g., magnetic particles may be provided in the implantable composition and vibrated to release the membrane-active agent, e.g., by heating the implantable composition, by bursting capsules that contain the membrane-active agent, etc.), infusion of chemical entities (e.g., acid or base, hypotonic or hypertonic salt, which disrupts the linkage between membrane-active agent and implantable composition to cause release of the membrane-active agent, etc.), thermal excitation to change diffusion kinetics or membrane transportation, weakening chemical linkages and modifying release, or combinations of the above.

The membrane-active-agent-releasing implantable composition may be, for example, in the form of membrane-active-agent-releasing particles. Such particles may come in various shapes including spherical and elongate shapes. Such particles may range from 10 nm to 10 mm in maximum cross-sectional dimension (e.g., diameter for a sphere).

The membrane-active-agent-releasing implantable composition may be, for example, in the form of a membrane-active-agent-releasing scaffold. Such scaffolds may come in various forms, including discs, rods, stents, coils, fiducial markers, woven meshes and tubes. Such scaffolds may contain pores ranging from 0.1 nm to 1 mm in size, or may not be porous at all.

The membrane-active-agent-releasing implantable compositions may be implanted into target tissue using any suitable implantation method including percutaneous placement of the implantable compositions, placement of the implantable compositions in or adjacent to one or more natural body lumens (e.g., blood vessels, including distal capillary or hyper-vascular lesions to embolize blood flow, gastrointestinal tracts, biliary ducts, lymph ducts, urinary tracts, or other body lumens), or a combination thereof. Placement of one or more implantable compositions in or adjacent to a natural body lumen may be conducted using a device such as a catheter, an endoscope, a microcatheter, a needle, or other flexible probes that maintain an open lumen.

As previously noted, in various aspects of the present disclosure, methods of treating a tissue volume are described that comprise (a) administering a membrane-active-agent-releasing implantable composition to a target site, such that the membrane-active agent is locally released to the tissue volume, and (b) performing IRE on the tissue volume.

In some embodiments, the implantable composition may be administered to the target site and IRE may be performed on the tissue volume in the same procedure. For example, the implantable composition may be administered to the target site and IRE may be performed on the tissue volume after allowing sufficient time to burst release to occur from the implantable composition into the tissue volume (e.g., ranging from 30 seconds to 180 minutes).

In some embodiments, IRE may be performed on the tissue volume in one or more procedures that are subsequent to the procedure in which the implantable composition is administered to the target site. For instance (e.g., where the implantable composition is a sustained release composition), one or more subsequent procedures may be performed at points in time ranging from 0.1 day to 6 weeks after administering the implantable composition to the target site.

As can be seen from the foregoing, an advantage of the compositions and methods of the present disclosure are that one can establish essentially any time course for membrane-active agent release that is desired and essentially any IRE schedule that is desired, which can be tuned based on tumor biology.

EXAMPLES

Materials. Roswell Park Memorial Institute (RPMI) 1640 medium, fetal bovine serum (FBS), Penicillin-Streptomycin (10,000 U/mL; 10,000 µg/mL), Dulbecco's phosphate buffered saline (DPBS), MTT (3-(4,5-dimethylthiazol-2-yl)-2,5-diphenyltetrazolium bromide) (MTT), dimethyl sulfoxide (DMSO), ethanol (200 proof), Alexa Fluor 488 NHS Ester were purchased from Thermo Fisher Scientific (Waltham, MA, USA). Hydroxlamine hydrochloride and PD-10 desalting columns (Sephadex G-25 medium; exclusion limit: $M_r$ 5000) were purchased from Millipore Sigma (Burlington, MA, USA). Electroporation cuvettes (4 mm gap) were from Harvard Apparatus (Holliston, MA, USA). UV transparent cuvettes (semi-micro, 1.5 mL) were purchased from USA Scientific (Ocala, FL, USA).

COMPUSYN Modeling of Drug Synergy. Combination index (CI) and dose reduction index (DRI) for each treatment combination were calculated by the Chou-Talalay method with the CompuSyn software program (ComboSyn Inc., Paramus, NJ, USA) (Chou, T. C. "Theoretical Basis, Experimental Design, and Computerized Simulation of Synergism and Antagonism in Drug Combination Studies." *Pharmacol. Rev.* 58, 621-681 (2006)). CI value is dimensionless quantification of drug interaction, CI=1 indicates an additive effect; CI<1 indicates a synergistic effect; CI>1 indicates an antagonistic effect. DRI is a measure of how much the dose of each drug can be reduced if used in combination at a given Fa as compared to the dose of each drug alone, DRI=1 indicates no dose reduction; DRI>1 indicates favorable dose reduction, DRI<1 indicates unfavorable dose reduction.

Statistical Analysis. ANOVA and Tukey HSD test for multiple comparisons were to determine the significance of difference in cell viability between different treatment groups. ANOVA and Tukey HSD test for multiple comparisons were to determine the significance of difference in fluorescence intensity of PAHM on coated microspheres. PAHM release profiles were fit with a two-phase exponential association model. All analyses were performed using GraphPad prism, version 9.0.0 (GraphPad software Inc., San Diego, California, USA).

Example 1. Poly(6-aminohexyl methacrylate) (PAHM) synthesis

Poly(6-aminohexyl methacrylate) (PAHM) was synthesized as follows: N-(tert-butoxycarbonyl) aminohexyl methacrylate (tBOCAHM) was initially synthesized as described in Zhu, C. et al. "Cationic methacrylate copolymers containing primary and tertiary amino side groups: Controlled synthesis via RAFT polymerization, DNA condensation, and in vitro gene transfection." *J. Polym. Sci. Part A Polym. Chem.* (2010). doi:10.1002/pola.24064. PAHM was then synthesized via atom transfer radical polymerization (ATRP) of tBocAHM followed by deprotection of the tBoc side chains based on a method reported by Ji, W. et al, "Poly(2-aminoethyl methacrylate) with Well-Defined Chain Length for DNA Vaccine Delivery to Dendritic Cells." *Biomacromolecules* 12, 4373-4385 (2011). The polymer was characterized using $^1H$ NMR and gel permeation chromatography (GPC) as described in Ji, W., "Ji, W. Synthetic polymers with well-defined structures for DNA vaccine delivery and cancer therapy." University of Minnesota Ph.D. dissertation. November 2013. The PAHM had a number-average molecular weight ($M_n$) of $2.08 \times 10^4$, Dispersity (Đ) of 1.26, and average degree of polymerization (DP) of 100.

Example 2. Bead Formation

Unhydrolyzed poly(methyl methacrylate) (PMMA) beads (90-106 µm in diameter) were coated with a membrane-active agent, specifically, poly(6-aminohexyl methacrylate) (PAHM), where n is an integer, by incubating beads in PAHM in ethanol, followed by evaporation of ethanol, as detailed further below.

Example 3. Fluorescence Labeling of PAHM

PAHM was fluorescently labeled with the NHS ester of Alexa Fluor 488 dye (Thermo Fisher Scientific) ($\lambda_{ex}/\lambda_{em}$: 494/517 nm; extinction coefficient=71,000 $cm^{-1}M^{-1}$) according to manufacturer's protocol. Theoretical degree of labelling was 1% based on feed ratio and 25-33% labelling efficiency (per manufacturer). Unreacted dye was removed by gel filtration with a PD-10 desalting column (Sephadex G-25 medium; exclusion limit: $M_r$ 5000) (Millipore Sigma). The purified fluorescently labeled PAHM solution was frozen at −80° C. overnight and lyophilized under 0.020 mBar for 4 days in a FreeZone® Freeze Dry System (Labconco, Kansas City, MO) equipped with a Maxima™ C Plus Vacuum Pump (Model M8c, Themo Fisher Scientific, Waltham, MA). Dried polymer was stored in a vacuum desiccator at room temperature (protected from light) until use.

Example 4. Optimizing Method of Coating Embolic Microspheres with PAHM

PMMA microspheres with average diameter 71 µm or 100 µm were provided by Boston Scientific Corporation (Maple Grove, MN, USA). PMMA microspheres were coated with PAHM by a solvent evaporation method. A mixture of fluorescently labeled and unlabeled PAHM (1:8 ratio of labeled:unlabeled) was dissolved in ethanol (Thermo Fisher Scientific) at total concentration of 0.1 mg/mL or 0.5 mg/mL. In glass vials, 1 mL PAHM solution was added to 50 mg PMMA microspheres (100 µm in diameter). Vials were placed uncovered on an orbital shaker (Lab-Line Instruments, Melrose Park, IL, USA) at room temperature for 3 days to evaporate the ethanol. Depending on the feed ratio, after drying, the microspheres were coated with PAHM at a concentration of 2 µg/mg or 10 µg/mg (µg PAHM/mg PMMA). Coated microspheres were stored in a vacuum desiccator at room temperature (protected from light) until use.

To optimize and speed up the coating process, PMMA microspheres were coated with PAHM using three different solvent evaporation methods. A mixture of fluorescently labeled and unlabeled PAHM (1:8 ratio of labeled:unlabeled) was dissolved in ethanol at total concentration of 0.8 mg/mL. 0.5 mL PAHM solution was added to 100 mg PMMA microspheres (100 μm in diameter) in glass vials. For coating method 1, ethanol was evaporated as described above (3 days on a slowly rotating orbital shaker). For coating method 2, uncovered vials were placed within a vacuum desiccator on top of a slowly rotating orbital shaker for 12 h. For coating method 3, ethanol was evaporated with compressed air for 10 min. Coated microspheres were stored in a vacuum desiccator at room temperature (protected from light) until use.

To visualize the PAHM coating, fluorescent and brightfield images of the coated microspheres were acquired with an Olympus IX70 inverted fluorescence microscope equipped with an Olympus DP72 camera and X-Cite 120 Wide-Field Fluorescence Microscope Excitation Light Source (Excelitas Technologies, Waltham, MA). Fluorescently labeled PAHM was visualized using an excitation wavelength of 480±50 nm and emission wavelength of 535±50 nm. The fluorescence intensity of the PAHM on individual coated microspheres was quantified using ImageJ, an open source, Java-based image processing program developed at the National Institutes of Health and the Laboratory for Optical and Computational Instrumentation (LOCI, University of Wisconsin).

Figure 1A:
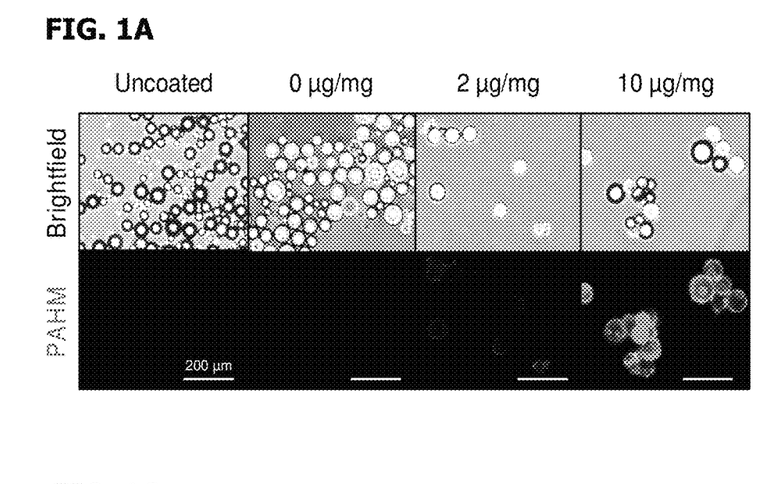
(FIG. 1A) Representative fluorescence microscopy images of microspheres coated with different amounts of PAHM (μg PAHM/mg PMMA).
Figure 1B:
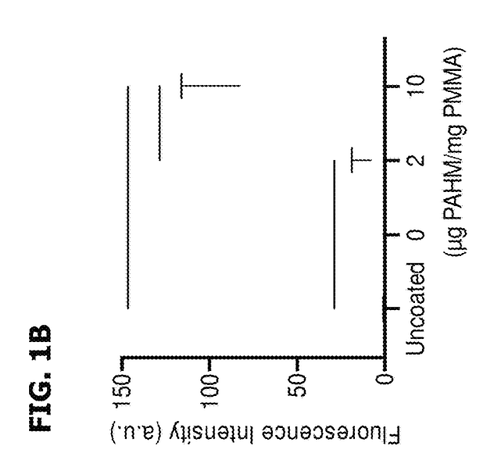

Embolic microspheres (100 μm in diameter) were coated with fluorescently labeled PAHM by a solvent evaporation method. Representative fluorescent micrographs (FIG. 1A) show that increasing the concentration of PAHM results in a thicker coating as microspheres coated with 10 μg/mg (μg PAHM/mg PMMA) showed 10.5-fold brighter fluorescence than microspheres coated with 2 μg/mg (μg PAHM/mg PMMA) (FIG. 1B).

Figure 1C:
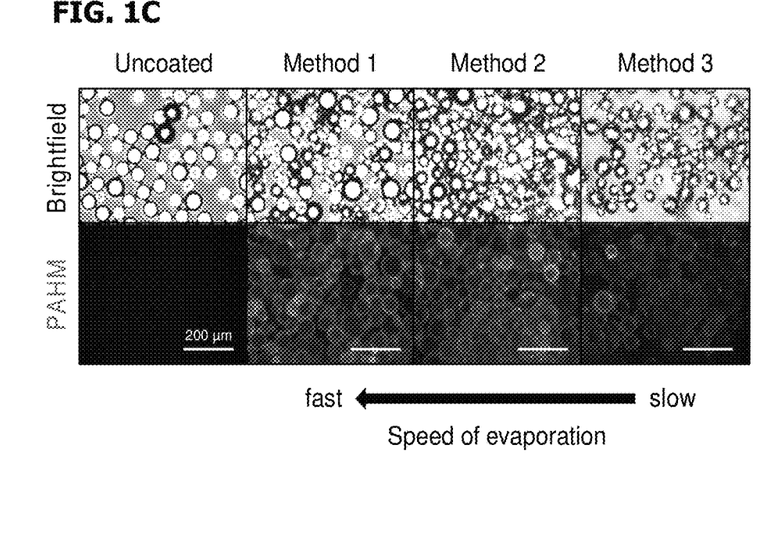
(FIG. 1C) Representative fluorescence microscopy images of microspheres coated with PAHM by different methods.
Figure 1D:
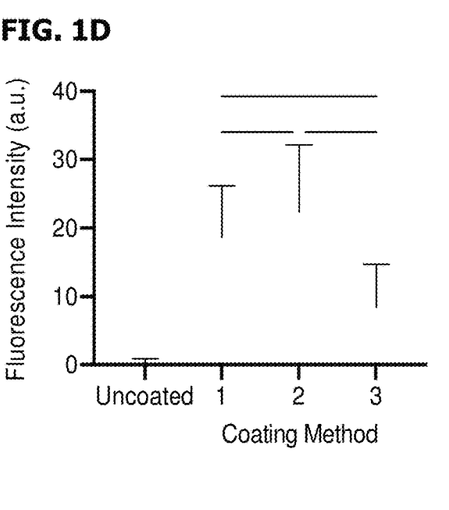
(FIG. 1D) Fluorescence intensity of PAHM on individual microspheres after coating by different methods. Data are shown as mean+/−SD (A) (n=16-63) (B) (n=165-186). ANOVA with Tukey HSD test (*$p<0.05$, $p<0.01$, *$p<0.001$, ****$p<0.0001$).

To optimize the coating process, embolic microspheres (100 μm in diameter) were coated with 4 μg/mg (μg PAHM/mg PMMA) fluorescently labeled PAHM by three different solvent evaporation methods. Representative fluorescent micrographs of microspheres coated by the three methods are shown in FIG. 1C and quantification of the fluorescence intensity is shown in FIG. 1D. In method 3, ethanol was quickly evaporated within 10 min which resulted in a bright, relatively uniform coating (FIG. 1C). In method 2, the slower evaporation of ethanol over 12 h seemed to slightly increase the amount of PAHM coated on the microspheres, as indicated by the 1.2-fold brighter fluorescence as compared to method 3 (FIG. 1D). However, further slowing the evaporation to 3 days in method 3 resulted in a much dimmer coating (FIG. 1C,D). We chose to use method 3 to coat microspheres for all subsequent experiments because it was fast while still generating a good coating.

All subsequent experiments (PAHM release kinetics and cytotoxicity assays) used microspheres coated with unlabeled PAHM at concentration of 10 μg/mg (μg PAHM/mg PMMA). PAHM was dissolved in ethanol at a concentration of 1 mg/mL. In glass vials, 1 mL PAHM solution was added to 100 mg microspheres (71 μm or 100 μm). Ethanol was evaporated using method 1 as described above.

Example 5. In Vitro Release Kinetics from Coated Microspheres

Figure 2A:
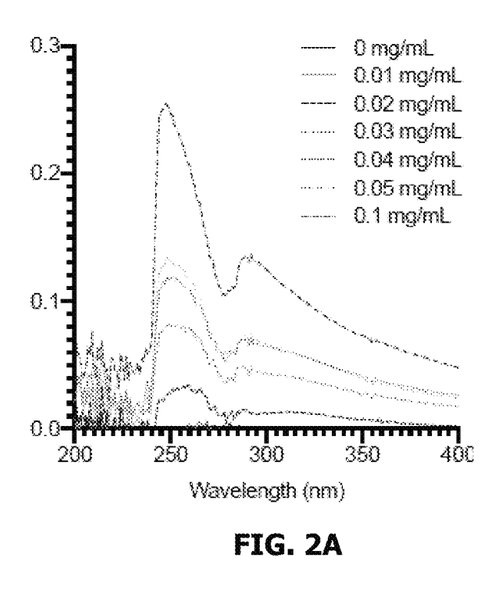
Figure 2B:
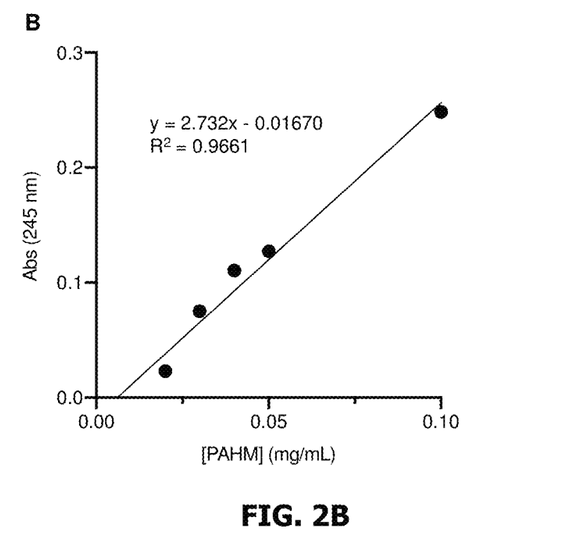

In 12-well plates, 25 mg coated microspheres (71 μm or 100 μm in diameter) were suspended in 1 mL cell culture medium (without phenol red) and were incubated in a humidified environment at 37° C. with 5% $CO_2$ for 1 week. At particular time points, 750 μL of the supernatant was sampled and replaced with fresh medium. The sampled supernatants were then diluted with 0.75 mL release medium (final volume: 1.5 mL) in UV transparent cuvettes (semi-micro, 1.5 mL) (USA Scientific, Ocala, FL, USA). The amount of PAHM in the supernatant was measured by measuring absorbance at 245 nm using a Cary 100 UV-Vis Spectrophotometer (Agilent Technologies, Santa Clara, CA, USA). FIGS. 2A and 2B illustrate quantification of PAHM in cell culture medium. FIG. 2A shows UV-Vis absorption spectra of different PAHM concentrations. FIG. 2B shows a calibration curve of absorbance at 245 nm vs. PAHM concentration.

Figure 3:
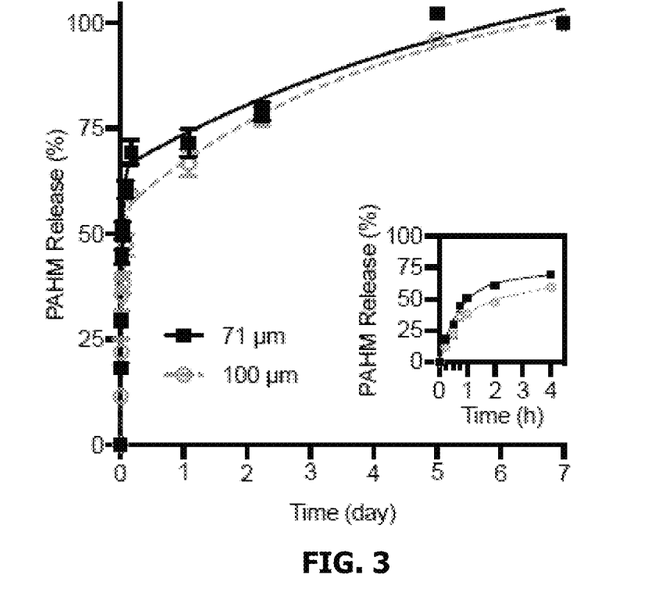
FIG. 3 shows release kinetics of PAHM from coated microspheres in cell culture medium at 37° C. Data are shown as mean+/−SD (n=4) and are fit with a two-phase exponential association model.

Release kinetic profiles were expressed as the cumulative percentage released over time and are illustrated in FIG. 3. After an initial burst release within the first 4 h, a sustained release of PAHM continued over the course of 1 week. PAHM was released slightly faster from 71 μm PMMA microspheres than 100 μm. Within the first hour, 51% and 38% of PAHM was released from 71 μm and 100 μm PMMA microspheres. After 4 h, 69% and 59% of PAHM was released from 71 μm and 100 μm PMMA microspheres. Over 20% of the PAHM was released from both sized microspheres between days 2 and 7.

Example 6. Cell Culture

Human pancreatic adenocarcinoma cell line AsPC-1 were obtained from ATCC. AsPC-1 cells were cultured in a medium consisting of Roswell Park Memorial Institute (RPMI) 1640 medium (Thermo Fisher Scientific, Waltham, MA, USA) with 2 g/L glucose, 2 mM L-glutamine, 2 g/L sodium bicarbonate, 10% heat inactivated fetal bovine serum (FBS) (Thermo Fisher Scientific), 100 U/mL penicillin (Thermo Fisher Scientific), and 100 μg/mL streptomycin (Thermo Fisher Scientific). AsPC-1 cells were cultured in tissue culture flasks and incubated in a humidified environment at 37° C. with 5% $CO_2$. When cells reached ~80% confluency the culture medium was removed, cells were harvested and split 1:3 to 1:6 to continue culture or used immediately for cytotoxicity experiments.

Example 7. Cytotoxicity of IRE in Combination with Free PAHM or PAHM Released from Coated Microspheres Harvested cells were centrifuged, and supernatant was discarded. Cell pellets were resuspended in cell culture medium (without phenol red), diluted to density of 675,000 cells/mL, and 1 mL aliquots were dispensed into 2 mL microcentrifuge tubes.

Free PAHM was dissolved in cell culture medium to an initial concentration of 250 μg/mL and diluted to varying concentrations. To the 1 mL cell suspensions, 0.5 mL PAHM dilutions were added to give final concentrations of 0-50 μg/mL. Coated microspheres (71 or 100 μm in diameter) and uncoated were suspended in cell culture medium to an initial concentration of 25 mg/mL and diluted to varying concentrations. To the 1 mL cell suspensions, 0.5 mL coated microsphere dilutions were added to give final concentrations of 0-5 mg/ml (corresponding to 0-50 μg/mL microsphere-coated PAHM).

After 15 min incubation, cells were treated with IRE as described in Shao, Q. et al. "Physical and Chemical Enhancement of and Adaptive Resistance to Irreversible Electroporation of Pancreatic Cancer." *Ann. Biomed. Eng.* 46, 25-36 (2018). Briefly, 400 µL prepared cell suspension was pipetted into an electroporation cuvette (BTX 45-0126, Harvard Apparatus, Holliston, MA) between the two aluminum plate electrodes (4 mm apart). The cuvette was placed in an external electric field created by an electric pulse generator (BTX ECM Square Wave Electroporation System, BTX Model No. 830, Harvard Apparatus, Holliston, MA, USA) which delivered 50 electrical pulses (100 µs pulse duration, 1 Hz frequency) at 150, 225, 300, 375, or 450 V (corresponding to electric field strengths of 375, 562.5, 750, 937.5, or 1125 V/cm).

For 15 min exposure time samples, 400 µL treated cell suspensions were transferred to microcentrifuge tubes, centrifuged, and supernatants were discarded. PAHM was washed away from cells with 1 mL Dulbecco's phosphate buffered saline (DPBS) (Thermo Fisher Scientific) (twice). Cell pellets were resuspended in 1 mL cell culture medium and plated in 12-well plates (180,000 cells/well). For 4 h and 24 h exposure time samples, 400 µL treated cell suspensions were plated into 12-well plates (180,000 cells/well) and 600 µL free PAHM or coated microsphere dilutions were added to maintain appropriate PAHM dose. After 4 h or 24 h incubation in a humidified environment at 37° C. with 5% $CO_2$ cells were washed with 1 mL DPBS (twice) and given 1 mL fresh cell culture medium.

Cell viability was evaluated using an MTT (3-(4,5-dimethyl-thiazol-2-yl)-2,5-diphenyl tetrazolium bromide) (Thermo Fisher Scientific) assay (Mosmann, T. "Rapid colorimetric assay for cellular growth and survival: Application to proliferation and cytotoxicity assays." *J. Immunol. Methods* 65, 55-63 (1983)). To each well, 100 µL MTT solution (5 mg/mL in DPBS) was added. After 4 h incubation in a humidified environment at 37° C. with 5% $CO_2$, 850 µL medium was removed from each well. Formazan crystals were dissolved in 1 mL DMSO (Thermo Fisher Scientific) and absorbance was measured at 540 nm using a BioTek Cytation 3 Cell Imaging Multi-Mode Reader (BioTek Instruments, Winooski, VT). Cell viability was determined by normalizing by the absorbance of untreated cells (with the same exposure time).

Figure 4A:
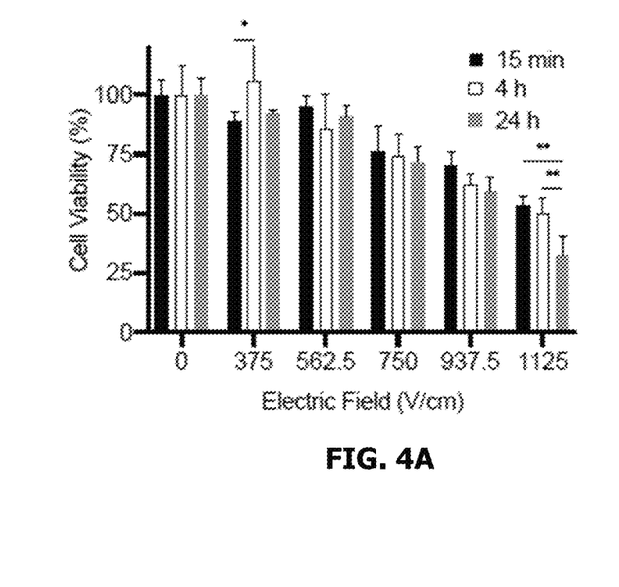
FIGS. 4A-4B show cell viability after (FIG. 4A) IRE or (FIG. 4B) PAHM treatment applied separately. Data are shown as mean+/−SD (FIG. 4A) (n=4-6) (FIG. 4B) (n=9-13). ANOVA with Tukey HSD test (*$p<0.05$, $p<0.01$, *$p<0.001$, ****$p<0.0001$).
Figure 4B:
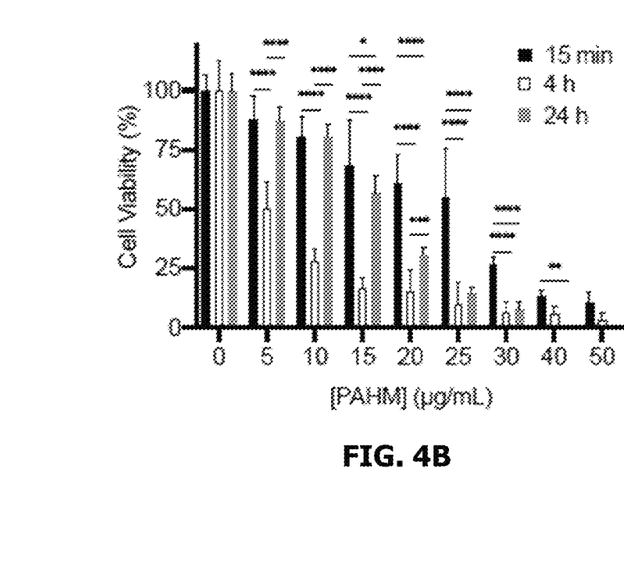

The viability of AsPC-1 cells after exposure to IRE or PAHM are shown in FIGS. 4A-4B. Higher electric field strengths led to lower cell viability after IRE alone, however, the reduction in cell viability was relatively modest (FIG. 4A). For cells exposed to 750 V/cm and below, over 70% of the cells remained viable. Even the highest electric field strength (1125 V/cm) only killed 46%, 50%, and 68% of cells at the 15 min, 4 h, and 24 h time points. In contrast, PAHM alone had a much more dramatic cell killing effect (FIG. 4B). For cells treated with PAHM at doses≥25 µg/mL, greater than 45%, 90%, and 85% of cells were killed when exposed continuously to PAHM for 15 min, 4 h, and 24 h. When treated with 40 µg/mL or 50 µg/mL PAHM for 24 h, 100% of the cells were killed.

The cell killing effect of IRE was seen to have little time dependence, as incubating the cells for 4 or 24 h post IRE treatment does not seem to influence cell viability (FIG. 4A). Only when exposed to 1125 V/cm did incubating the cells for 24 h result in lower cell viability. Contrary to IRE, cell killing by PAHM was dependent on the exposure time. Interestingly, treating cells with PAHM for 4 h appears to result in lower cell viability than treating cells for 24 h. At PAHM doses≤20 µg/mL, there was a significant reduction in cell viability for 4 h exposure time, but cells appeared to somehow recover after 24 h. At PAHM doses≥25 µg/mL, this recovery was not seen as there was no statistically significant differences in cell viability for the 4 h and 24 h exposure times.

Figure 5A:
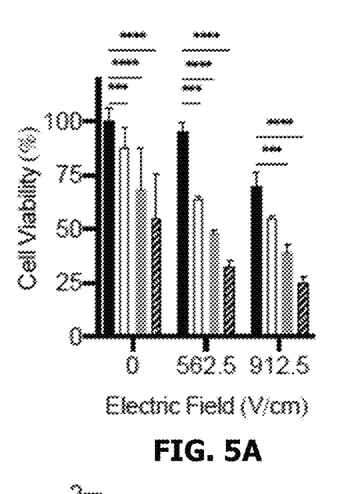
Figure 5B:
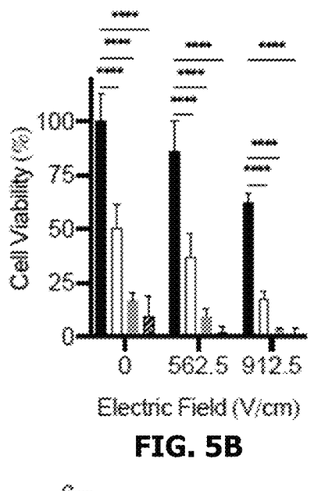
Figure 5C:
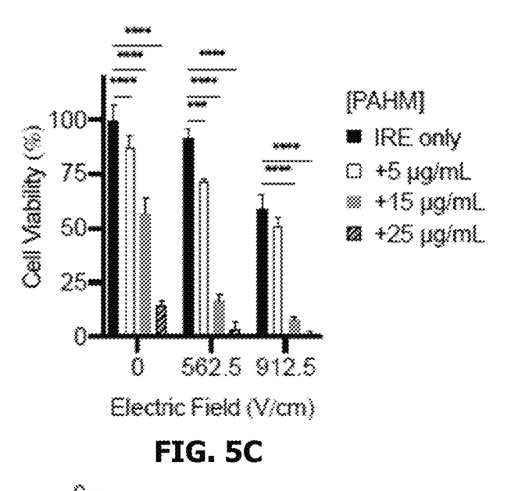

To evaluate the ability of PAHM to enhance the cell killing effect by IRE, two electric field strengths were combined with three PAHM doses (FIGS. 5A-5C). For all exposure times, combining PAHM with IRE resulted in significantly more cell death. When only treating cells with PAHM for 15 min, the viability of cells exposed to 562.5 V/cm dropped from 95% down to 64%, 48%, and 33% for 5 µg/mL, 15 µg/mL, and 25 µg/mL PAHM (FIG. 5A). For 4 h exposure to PAHM, the viability of cells exposed to 562.5 V/cm dropped from 86% to 37%, 10%, and 2% for 5 µg/mL, 15 µg/mL, and 25 µg/mL PAHM (FIG. 5B). Similar to PAHM treatment alone, there is some cell viability recovery for cells treated with IRE and PAHM for 24 h; however, the viability of cells exposed to 562.5 V/cm still dropped from 91% to 72%, 17%, and 3% for 5 µg/mL, 15 µg/mL, and 25 µg/mL PAHM (FIG. 5C).

Figure 5D:
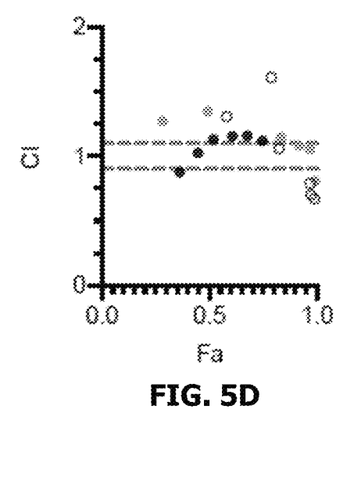
(FIG. 5D) Combination index analysis (CI<1, =0.9-1 (dashed lines), >1 indicates synergism, nearly additive effect, and antagonism, respectively). Dose reduction index analysis for (FIG. 5E) IRE and (FIG. 5F) PAHM (DRI<1, =1 (dashed line), >1 indicates unfavorable dose reduction, no dose reduction, favorable dose reduction, respectively).
Figure 5E:
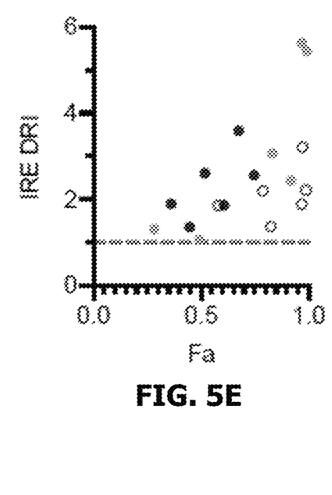
Figure 5F:
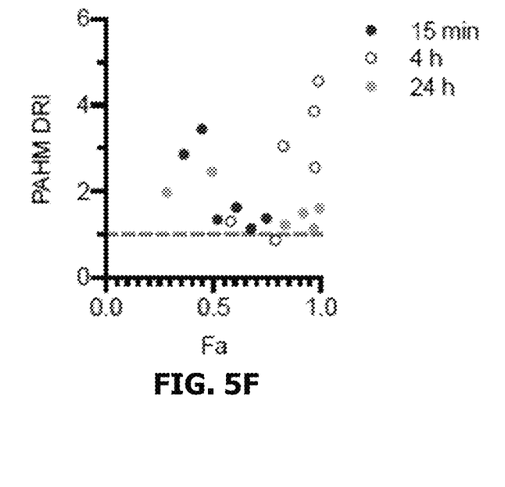

To examine the ability of PAHM to enhance the efficacy of IRE, the Combination Index (CI) and Dose Reduction Index (DRI) for each combination of IRE and PAHM were calculated by the Chou-Talalay method with the CompuSyn software program (ComboSyn Inc., Paramus, NJ). The CI are plotted against the fractional affect (Fa), the fraction of cell growth inhibited by a particular combination of IRE and free PAHM in FIG. 5D. For 15 min PAHM exposure, the combination of IRE and free PAHM appears to be slightly antagonistic as a majority of the CI are greater than 1.12. At longer PAHM exposure, the CI tends to decrease at higher Fa. For 4 h PAHM exposure, the combinations with the three highest Fa appear to be synergistic. For 24 h PAHM exposure, combinations with lower Fa displayed slight to moderate antagonism; however, combinations with higher Fa are nearly additive or display moderate synergy. The DRI of IRE electric field strength and PAHM dose are shown in FIG. 5E and FIG. 5F. The DRI of IRE tends to increase with Fa for all three exposure times and all DRI are greater than 1. This indicates that for any combination with PAHM, a lower electric field strength can kill an equivalent fraction of cells as a higher electric field strength alone. The DRI of PAHM for all but one combination are greater than 1, indicating the PAHM dose can also be reduced when used in combination. For 15 min and 24 h exposure the DRI tends to decrease with Fa; however, the DRI tends to increase with Fa for 4 h exposure to PAHM.

Figure 6A:
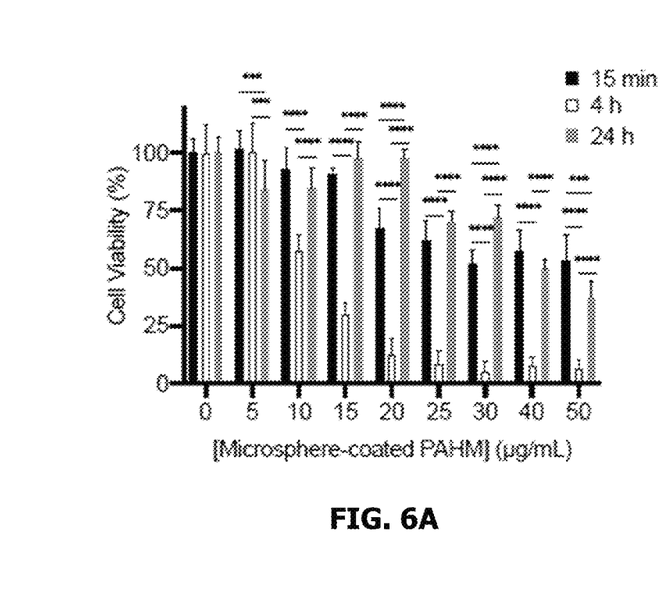
FIGS. 6A-6B show cell viability after exposure to PAHM released from coated microspheres with average diameter (FIG. 6A) 71 μm (FIG. 6B) 100 μm. Data are shown as mean+/−SD (n=6-12), ANOVA with Tukey HSD test (*p<0.05, p<0.01, p<0.001, **p<0.0001).
Figure 6B:
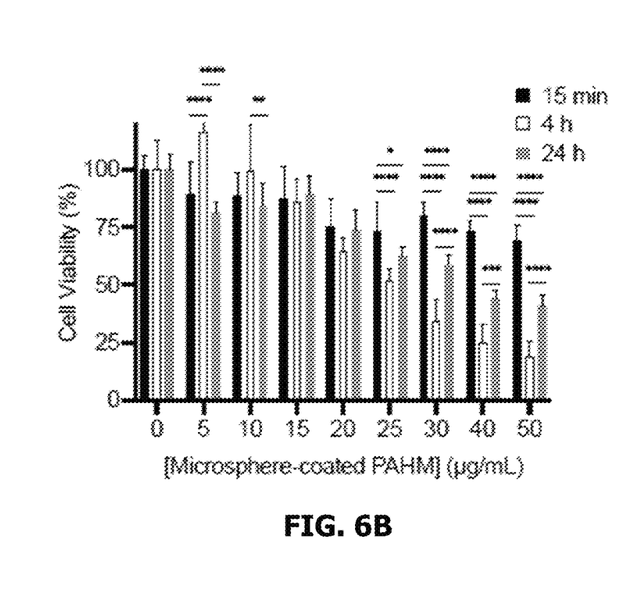
Figure 7:
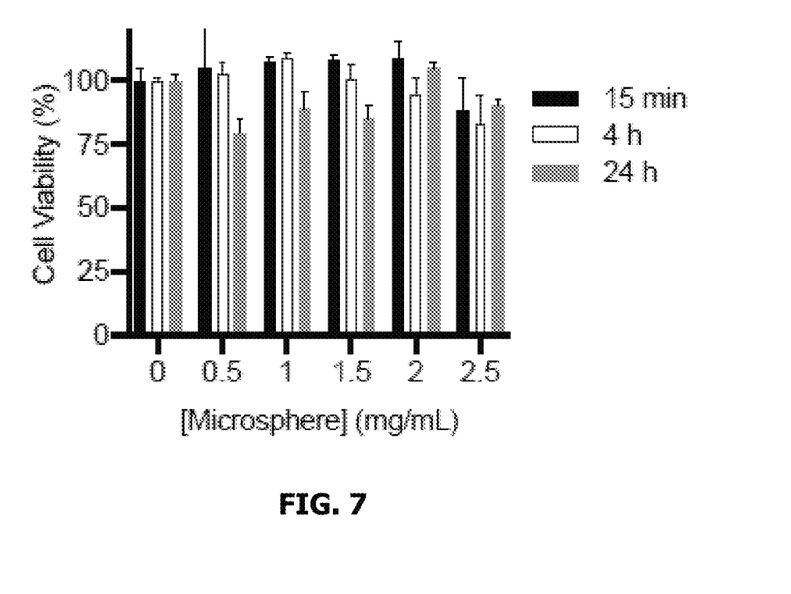
FIG. 7 shows cell viability after exposure to uncoated embolic microspheres. Data are shown as mean+/−SD (n=2).

The viability of AsPC-1 cells after exposure to microspheres (71 µm or 100 µm in diameter) coated with 10 µg/mg (µg PAHM/mg PMMA) are shown in FIGS. 6A-6B. As PMMA microspheres alone (uncoated) show little to no toxicity (FIG. 7), all cell killing is attributed to PAHM released from the coated microspheres. Similar to free PAHM, the exposure time to PAHM released from 71 µm coated microspheres had a significant effect on cell viability (FIG. 6A). Only moderate cell killing resulted after 15 min exposure to 71 µm coated microspheres as even the highest dose (50 µg/mL microsphere-coated PAHM) only killed 47% of cells. Exposure to 71 µm coated microspheres for 4 h greatly reduced cell viability. For ≥20 µg/mL microsphere-coated PAHM, less than 13% of the cells were viable. The cells regained much of their viability after 24 h exposure to 71 µm coated microspheres, similar to the viabilities seen after 15 min exposure. Only for 50 µg/mL microsphere-coated PAHM did 24 h exposure kill statistically significant more cells than 15 min exposure. Similar results were seen for cells treated with 100 µm coated microspheres for 15 min or 24 h; however, 4 h exposure did not result in nearly as much cytotoxicity (FIG. 6B). Even at 50 μg/mL microsphere-coated PAHM, 19% cell viability remained after 4 h exposure to 100 μm coated microspheres. Only for ≥25 μg/mL microsphere-coated PAHM did longer exposure time result in significantly lower cell viability than 15 min exposure.

Figures 8A, 8B, 8C, 8D, 8E, 8F:
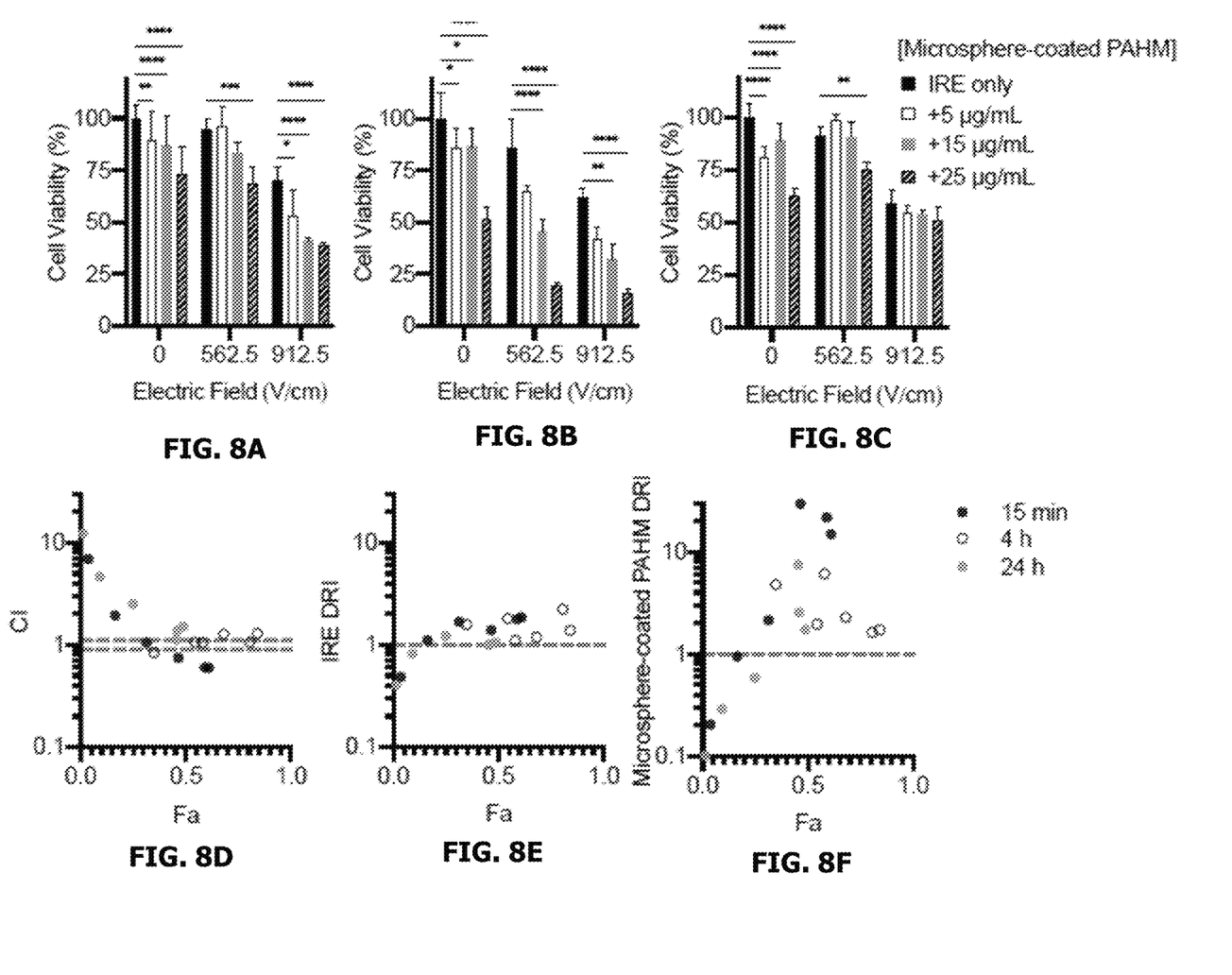

Example 8. Cytotoxicity of IRE in Combination with PAHM Released from Coated Microspheres Due to the slower release of PAHM and the much smaller differences in cell viability between 4 h and 24 h exposure times, 100 μm coated microspheres were chosen to examine the ability of PAHM released from coated microspheres to enhance IRE (FIGS. 8A-8F). Released PAHM did enhance the cell killing effect of IRE after 15 min and especially 4 h; however, 24 h exposure time did not significantly reduce cell viability. For 15 min exposure, the viability of cells exposed to 912.5 V/cm decreased from 95% down to 40-54% when coated microspheres were added; however, there were no statistically significant differences between the three microspheres doses (FIG. 8A). The most substantial IRE enhancement was seen at 4 h exposure to 100 μm coated microspheres, as the viability of cells exposed to 562.5 V/cm was reduced from 86% to 65%, 56%, and 19% for 5 μg/mL, 15 μg/mL, and 25 μg/mL microsphere-coated PAHM (FIG. 8B). This enhancement largely disappeared after 24 h exposure. The only combination to significantly reduce cell viability when compared to IRE alone was an electric field strength of 562.5 V/cm and 25 μg/mL microsphere-coated PAHM (FIG. 8C). This reduction was also relatively moderate, from 91% for IRE alone to 75% for the combination.

The CI and DRI for the combinations of IRE and coated PMMA microspheres were also calculated. As shown by the CI in FIG. 8D, combining IRE with exposure to PAHM released from coated microspheres for 15 min is strongly antagonistic at low Fa, but the combination becomes synergistic at intermediate Fa. For 4 h exposure, most of the CI are within (or close to) the 0.9-1.1 range which indicates a nearly additive effect. All 24 h exposure time combinations displayed CI greater than 1.1. At low Fa the combinations are strongly antagonistic, but the antagonism tends to decrease with Fa. The DRI of IRE electric field strength and microsphere-coated PAHM dose are shown in FIG. 11E and FIG. 11F. The DRI for IRE tends to increase with Fa for all three exposure times and for Fa>0.1, the DRI for IRE are all greater than 1. The DRI for microsphere-coated PAHM tends to increase with Fa for 15 min and 24 h exposure time but decrease with Fa for 4 h exposure time. For Fa>0.2, the DRI for microsphere-coated PAHM are greater than 1.

The invention claimed is:

1. A method of treating a tissue volume comprising (a) administering an implantable composition comprising a releasable membrane-active agent to a target site such that the membrane-active agent is locally released to the tissue volume and (b) performing treatment of the tissue volume by application of a pulsed electric field to the tissue volume, wherein the implantable composition is an embolic composition comprising the releasable membrane-active agent, wherein the releasable membrane-active agent is selected from amino alkyl acrylates, amino alkyl methacrylates, copolymers of amino alkyl acrylates with alkyl acrylates, and copolymers of amino alkyl methacrylates with alkyl methacrylates.

2. The method of claim 1, wherein the treatment results in irreversible electroporation, reversible electroporation or thermal treatment.

3. The method of claim 1, wherein the tissue volume corresponds to all or part of a tumor or to all or part of a tumor and healthy tissue surrounding the tumor.

4. The method of claim 3, wherein the tumor is selected from tumors of the pancreas, breast, lung, prostate, liver, kidney, brain, uterus, ovary, stomach, duodenum, or skin.

5. The method of claim 1, wherein the embolic composition is administered to one or more blood vessels that supply blood the tissue volume or wherein the embolic composition is administered percutaneously or endoscopically via injection.

6. The method of claim 1, wherein the implantable composition is at least partially biostable or is bioabsorbable.

7. The method of claim 1, wherein the implantable composition is a solid implantable composition when administered to the target site or wherein the implantable composition is a liquid composition that becomes a solid implant upon introduction when administered to the target site.

8. The method of claim 7, wherein the solid implantable composition is an implantable particle, or wherein the solid implantable composition is a scaffold.

9. The method of claim 7, wherein the solid implantable composition is an implantable particle that ranges from 10 nm to 10 mm in maximum cross-sectional dimension, or wherein the solid implantable composition is a scaffold selected from a disc, a rod, a stent, a coil, a fiducial marker, a plate, a tube, or a semi-permeable woven mesh.

10. The method of claim 7, wherein the membrane-active agent is present throughout the solid implantable composition, wherein the membrane-active agent is present in only a portion of the solid implantable composition, wherein the membrane-active agent is present at a surface of the solid implantable composition but is not is present in a bulk of the solid implantable composition, wherein the membrane-active agent is present in a bulk of the solid implantable composition but is not is present at a surface of the solid implantable composition, wherein the membrane-active agent is homogeneously present the solid implantable composition, wherein the membrane-active agent is present in a concentration gradient the solid implantable composition, wherein the membrane-active agent is present in one or more layers disposed on an underlying substrate material, wherein the membrane-active agent is encapsulated within an encapsulating material, or wherein the membrane-active agent is dispersed within a matrix material.

11. The method of claim 7, wherein the solid implantable composition is an embolic particle; and wherein the membrane-active agent is coated on or infused into the embolic particle or is conjugated to the embolic particle via a covalent linkage.

12. The method of claim 1, wherein release of the membrane-active agent is triggered by electrical pulses, ultrasound, magnetic field variations, or thermal inputs.

13. The method of claim 1, wherein the treatment is performed in a same procedure as administration of the implantable composition.

14. The method of claim 1, wherein the treatment is performed in a procedure subsequent to administration of the implantable composition.

15. The method of claim 1, wherein the treatment is performed in a procedure at a time ranging from the same day up to 30 days after administration of the implantable composition.

16. The method of claim 1, wherein one or more electrodes for the treatment are placed within or adjacent to the tissue volume.

17. The method of claim 1, (a) wherein one or more electrodes for the treatment are placed adjacent the tissue volume at one or more locations on the skin, (b) wherein one or more electrodes for the treatment are percutaneously placed within or adjacent to the tissue volume, (c) wherein one or more electrodes for the treatment are placed within or adjacent to the tissue volume via a device that is inserted into one or more natural body lumens, or
 (d) a combination of any two or all three of the preceding placement techniques.

\* \* \* \* \*